United States Patent [19]
Schafer

[11] Patent Number: 5,993,422
[45] Date of Patent: Nov. 30, 1999

[54] DEVICE FOR DOSING MEDICINAL FLUIDS

[75] Inventor: Helmut Schafer, Usingen, Germany

[73] Assignee: Fresenius AG, Germany

[21] Appl. No.: 09/017,845

[22] Filed: Feb. 3, 1998

[30] Foreign Application Priority Data

Feb. 4, 1997 [DE] Germany .................... 297 01 861

[51] Int. Cl.[6] .................................................. A61M 37/00
[52] U.S. Cl. .................... 604/154; 604/151; 128/DIG. 1; 417/22
[58] Field of Search ................... 604/151, 152, 604/154, 155; 120/DIG. 1; 471/22

[56] References Cited

U.S. PATENT DOCUMENTS

| | | | |
|---|---|---|---|
| 3,447,479 | 6/1969 | Rosenberg . | |
| 4,396,305 | 8/1983 | Kelly et al. ........................... | 604/152 |
| 4,450,079 | 5/1984 | Farr ..................................... | 604/152 |
| 4,636,431 | 1/1987 | Whitney et al. ..................... | 604/155 |
| 4,798,589 | 1/1989 | Tsco .................................... | 604/152 |
| 5,492,535 | 2/1996 | Reed et al. .......................... | 604/152 |
| 5,656,034 | 8/1997 | Kochersperger et al. ........... | 604/155 |

FOREIGN PATENT DOCUMENTS

| | | |
|---|---|---|
| 0 193 266 | 9/1988 | European Pat. Off. . |
| 0 296 124 | 12/1988 | European Pat. Off. . |
| 10 26 047 | 3/1958 | Germany . |
| WO 93/14797 | 8/1993 | WIPO . |
| WO 97 45150 | 12/1997 | WIPO . |

*Primary Examiner*—Corrine McDermott
*Assistant Examiner*—Kent Gring
*Attorney, Agent, or Firm*—Heslin & Rothenberg, P.C.

[57] ABSTRACT

A device for dosing medicinal fluids, in particular a feeding solution for enteral alimentation, has a pump unit (2) with a displacement element (15) and a drive unit (3) for the displacement element. The pump unit (2) can be separated from the drive unit (3) and is realized in the form of a non-reusable, disposable item. After the device has been used, the pump unit is simply replaced with a new pump unit, so that it is unnecessary to clean the parts of the dosing device that carry the fluid.

14 Claims, 4 Drawing Sheets

DEVICE FOR DOSING MEDICINAL FLUIDS

BACKGROUND OF THE INVENTION

1. Field of the Invention

This invention concerns a device for dosing medicinal fluids, in particular a nutrient solution for enteral alimentation. The invention further relates to a system for enteral alimentation using such a device for dosing the nutrient solution.

2. Description of Related Art

A device for the dosed dispensing of a medicinal fluid, for example a medication, is described in WO 93/14797. The medication pump has a two-part housing, the two elements of which are held together by threaded fasteners and hold a collapsible container filled with the medicinal fluid. In the housing, pressure is applied to the fluid bag by a spring-loaded plate, as a result of which the fluid is discharged from the container via a hose or similar flexible line.

According to the prior art, patients suffering from malnutrition are treated by administration of a nutrient solution from a container via a hose and a stomach tube that has been inserted in the patient's gastrointestinal tract. For long-term patients, mobile feeding systems are used, with which the patient can essentially move around freely, except for the fact that he has to take all the equipment required for mobile feeding with him. This equipment includes the container that contains the nutrient solution, which has a connector for the delivery system for the nutrient solution, the delivery device, and a peristaltic pump to continuously deliver the nutrient solution at a specified rate, into which the feeding tube of the delivery unit is inserted. The advantage of the hose pump is that the medicinal fluid does not come into contact with the components of the pump.

The feeding systems of the prior art have proven successful in praxis, but one disadvantage of these systems is that, on account of their size and the relatively heavy weight of the equipment required, the patients find them difficult to use during ambulatory treatment. Moreover, the hose pump is relatively expensive to manufacture.

BRIEF SUMMARY OF THE INVENTION

The object of the invention is to create a device for dosing medicinal fluids, in particular a nutrient solution for enteral alimentation, which is compact, easy to handle, and economical to operate.

The invention accomplishes this object by means of the features listed in claim 1.

The device claimed by the invention for dosing medicinal fluids is not constructed like a hose pump. The medicinal fluid is transported by means of a positive displacement device that is located in a pump chamber. Although the medicinal fluid comes into contact with components of the dosing device, the tedious and time-consuming cleaning of the parts that transport the fluid is rendered unnecessary, because the parts that come in contact with the fluid can easily be replaced after the device has been used only once. These parts are non-reusable, disposable items that can be manufactured economically in large quantities. The relatively expensive drive unit of the displacement element, on the other hand, is designed to be re-used. The displacement element can be constructed, for example, in the form of a rotary displacement pump or in the form of a piston displacement pump.

The dosing device of the invention has two housing parts that can be separated from one another, one part of which holds the pump chamber with the displacement element and the other of which holds the drive unit for the displacement element. The torque is transmitted by means of coupling elements that are engaged when the drive unit is coupled.

In one preferred embodiment, the drive unit has a motor that is driven by means of a wind-up coil spring. The dosing device can in this way be operated independently of the electrical power supply system or batteries, which means that it is ready to be used at any time. It is also possible, however, to operate the displacement element by means of a battery-powered electric motor.

To vary the delivery rate, the drive unit preferably has a transmission with an adjustable gear ratio. To provide a lower or higher delivery rate, the transmission can also be designed in the form of a module that can be replaced with a transmission that has a different gear ratio.

The two parts of the housing are preferably connected to one another by means of threaded connections. A bayonet connection, for example, can also be used to connect the housing parts to one another. The drive unit can also be realized in the form of a plug-in module, however.

In an additional preferred embodiment of the invention, the pump chamber is cylindrical and the displacement element is a body which can rotate in the cylindrical pump chamber and has a plurality of wing-like displacement elements that are in tight contact with the cylinder wall. This type of construction is particularly simple, which keeps the manufacturing costs low. For example, the displacement element and the housing body can be manufactured in large quantities in the form of injection-molded parts, and the displacement element can be inserted in the cylindrical pump chamber, which is then closed by the housing part that holds the displacement element drive system.

In one advantageous configuration, when the drive unit is coupled, the output shaft of the drive unit forms a positive or form-fitting connection with the displacement element. The displacement element advantageously has a central recess with an internal contour, while the output shaft that is engaged in the recess is provided with a matching external contour.

In an additional advantageous embodiment, the displacement element is a piston that can move inside a cylindrical pump chamber, whereby the inlet and outlet are located on one end of the pump chamber, and there is an inlet valve in the inlet and an outlet valve in the outlet.

The piston is advantageously driven by means of a slide that carries a pin which can move back and forth, and which, when the drive unit is coupled, is engaged in the recess of a piston rod that is connected to the piston of the pump unit.

In the above embodiment, the housing part of the drive unit preferably has a receptacle into which the pump unit can be inserted, and in which it fits so that it can be fixed in position.

A particularly simple and economical manufacture of the pump unit in the form of a non-reusable, disposable item becomes possible if the housing part is realized in the form of a Y-shaped tubular piece, the branches of which form the inlet and outlet tubes respectively of the pump chamber. The Y-shaped tubular piece can easily be positioned in the receptacle by means of suitable contact surfaces.

To facilitate the connection, the wall of the housing part of the drive unit in the vicinity of the receptacle is advantageously realized so that there is an opening through which the inlet and outlet tubes of the pump unit are accessible from the outside.

The dosing device can advantageously be used to dispense a nutrient solution fed from a container via a feeding tube to a stomach tube that is introduced into the patient's stomach. The dosing device is thereby connected to the feeding tube. To connect the ends of the hose, there are preferably connectors on the dosing device, e.g. the Luer Lock connectors, which are widely used on medical equipment, or the funnel connectors, which are frequently found on conventional hose systems.

Compared to the enteral alimentation systems of the prior art, in which the nutrient solution is transported only by gravity, a system in which the feeding tube is connected to the dosing device claimed by the invention has the advantage that the delivery rate is largely independent of the viscosity of the nutrient solution and the volume of liquid in the reservoir. Compared to feeding systems that use the peristaltic pumps of the prior art, there is no danger that the pump hose will ultimately become fatigued, which can result in changes in the delivery rate. An additional advantage is in the compact construction, which gives the patient more freedom during ambulatory feeding through a stomach tube. It is also no longer necessary to rinse the dosing device after it has been used, because the pump unit is a non-reusable, disposable item. Because the drive unit is reusable, the dosing device can be operated economically.

BRIEF DESCRIPTION OF THE DRAWINGS

One exemplary embodiment of the invention is explained in greater detail below, with reference to the accompanying drawings.

DETAILED DESCRIPTION

Figure 1:
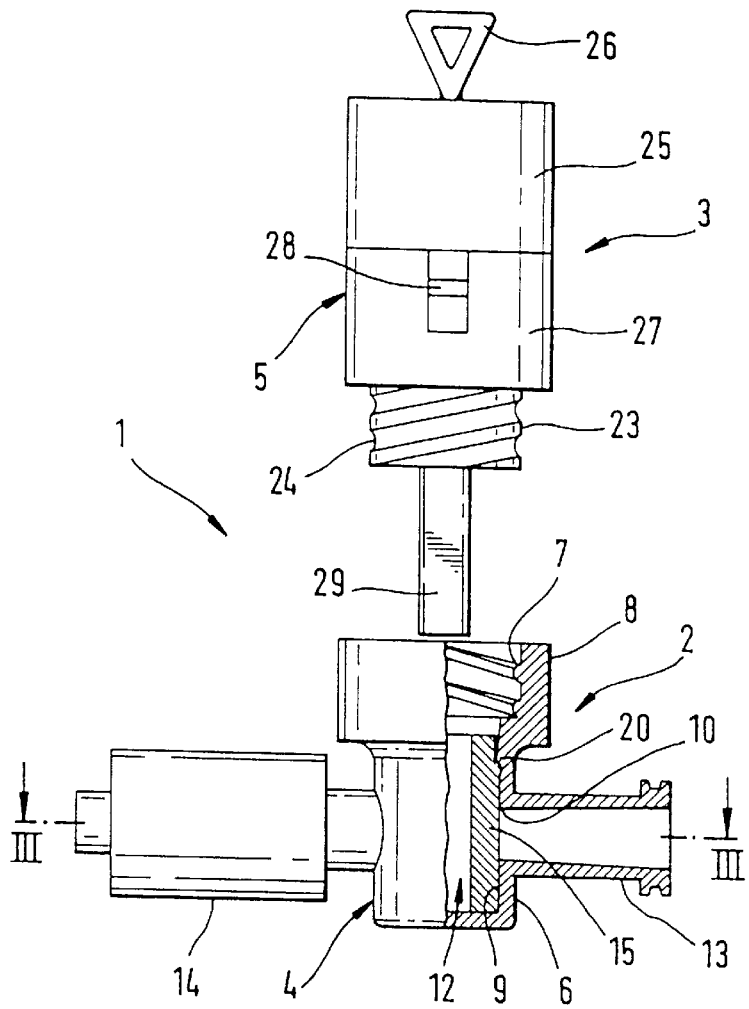
FIG. 1 shows in a partial cross section a preferred embodiment of the invention for the dosing of medicinal fluids, whereby the drive unit is unscrewed from the pump unit.
Figure 2:
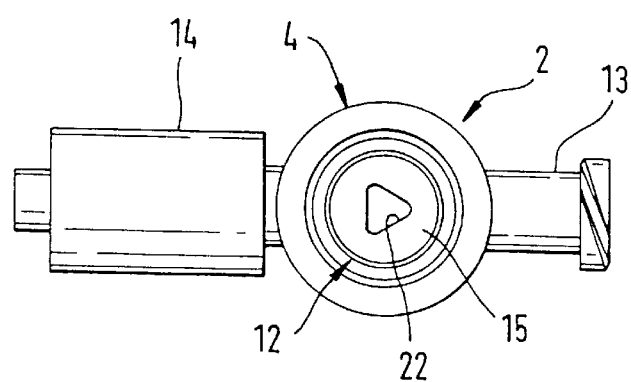
FIG. 2 shows the pump unit of the dosing device in an overhead view.
Figure 3:
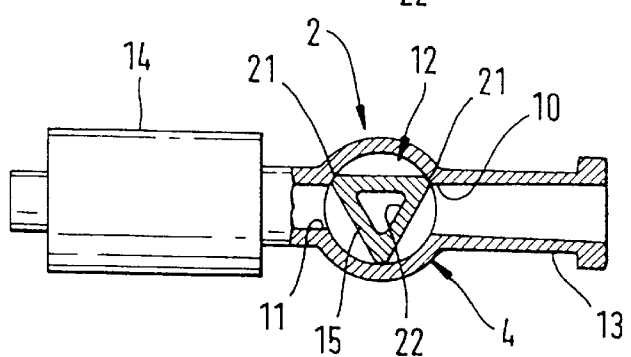
FIG. 3 shows a section through the pump unit of the dosing device along Line III—III in FIG. 1.

FIG. 1 shows the dosing device 1 in a partial cross section, in which it consists of a pump unit 2 that is realized in the form of a non-reusable, disposable item and a drive unit 3 that can be reused, whereby the housing part 4 of the pump unit and the housing part 5 of the drive unit are held together by threaded connections.

The housing part 4 of the pump unit 2 comprises a hollow cylindrical body 6 that is closed on one end, and is provided on the other end with a fastening flange 8 that has a female thread 7. In the cylinder wall 9, there are two borings that are offset from one another on the periphery by 180°, whereby the boring designated 10 forms the inlet and the boring designated 11 forms the outlet of the cylindrical pump chamber 12. For the connection of a hose line system, the pump unit 2 has a Luer Lock outer cone 14, which is connected to the inlet, and a Luer Lock inner cone 13, which is connected to the outlet, both of which are integral components of the housing part 4. The Luer Lock connectors 13, 14 lie on a common axis which runs at a right angle to the longitudinal axis of the pump chamber 12.

Figure 4:
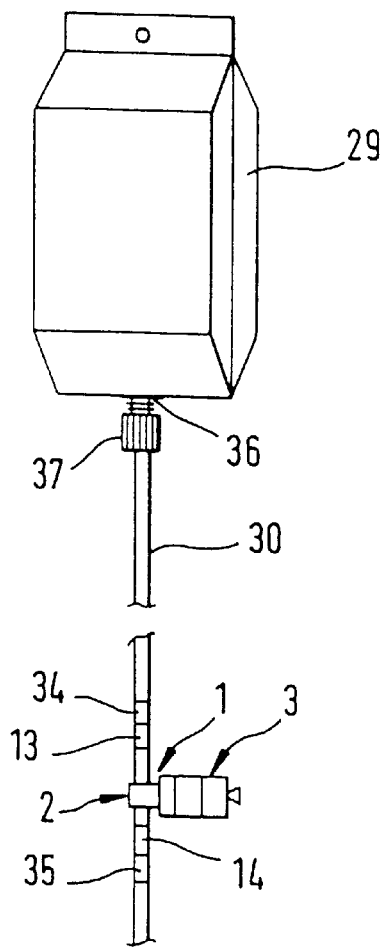
FIG. 4 shows the displacement element of the pump unit in a partial cross section.
Figure 4:
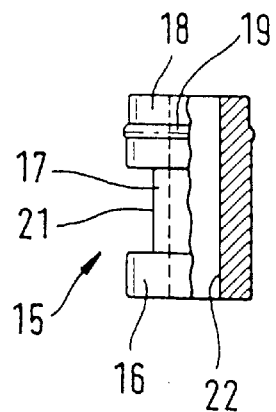

During the operation of the dosing device, a rotating displacement element 15 that is realized in the form of an insertable part (FIG. 4) sits in the cylindrical pump chamber 12 of the housing part 4. The displacement element 15 has a cylindrical lower segment 16, a central segment 17, which is essentially triangular in cross section, and a cylindrical upper segment 18. In the cylindrical pump chamber 12, the displacement element 15 is prevented from slipping out by an encircling shoulder 19 on its upper cylindrical segment 18, by means of which shoulder the displacement element sits on an encircling projection 20 in the cylinder wall 9. The rounded corners 21 of the central segment 17, which is triangular in cross section, are in tight contact with the cylinder wall 9. The displacement element 15 also has an axial recess 22 with a triangular contour.

The housing part 5 of the drive unit 3 has a cylindrical shoulder 23 with a male thread 24 that can be screwed to the fastening flange 8 of the pump unit 2 and holds a motor 25 that is operated by a windup coil spring. The motor in question is a spring-wound motor, such as those used in timepieces or similar devices, and is not illustrated in any particular detail. To wind up the coil spring, there is a fold-out screw 26 in the housing cover. Downstream of the motor 25 there is a transmission 27 that has an adjustable gear ratio. The gear ratio is selected by means of a slide switch 28 that is integrated into the housing part 5, whereby one of three different speeds can be selected. The output shaft 29 of the transmission 27 extends through the cylindrical housing shoulder 23 and has a triangular cross section, which matches the cross section of the axial recess 22 in the displacement element 15. When the two housing parts 4, 5 are screwed together, the output shaft 29 is engaged in the recess 22 of the displacement element, so that the torque can be transmitted to the displacement element.

Figure 5:
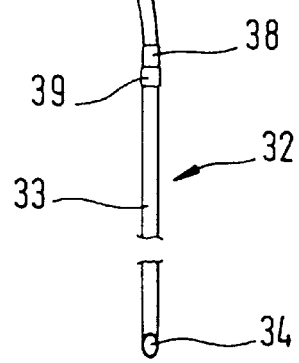
FIG. 5 shows a system for enteral alimentation in which the feeding hose is connected to the dosing device.

FIG. 5 shows a system for enteral alimentation in which the device for dosing the nutrient solution is used. The system comprises a container 29 that holds the nutrient solution, a first tube 30, the dosing device 1, a second tube 31, and a stomach tube 32, which has a stomach tube hose 33 that is introduced into the patient's stomach. The distal end of the stomach tube hose is provided with an olive-shaped body 34 that is open on the end and/or on the side. The dosing device 1 is connected by means of Luer Lock connectors 34, 35 to the respective ends of the tube, which are connected by means of the corresponding Luer Lock connectors to the dosing device 1. The container 29 has a bottom connector 36 with a membrane that can be pierced by a spike, which is an integral part of the connector 37 of the first tube 30. The connection between the second tube 31 and the stomach tube 32 is made by means of Luer Lock connectors 38, 39.

During operation, the dosing device 1 is located underneath the bag 29 that contains the nutrient solution, so that the liquid flows by the force of gravity through the first tube 30 into the pump chamber 12 of the dosing device. As a function of the speed of rotation of the rotary displacement element 15, the nutrient solution is transported via the second tube into the stomach tube hose 33, whereby the rate of delivery can be changed by selecting a different gear ratio.

After use, the drive unit 3 of the dosing device 1 is unscrewed from the pump unit 2 and the Luer Lock connector connections between the dosing device and the feeding tubes 30, 31 are detached. The pump unit 2 through which the nutrient solution has been transported can be replaced with a new unit, which makes cleaning unnecessary.

Figure 6:
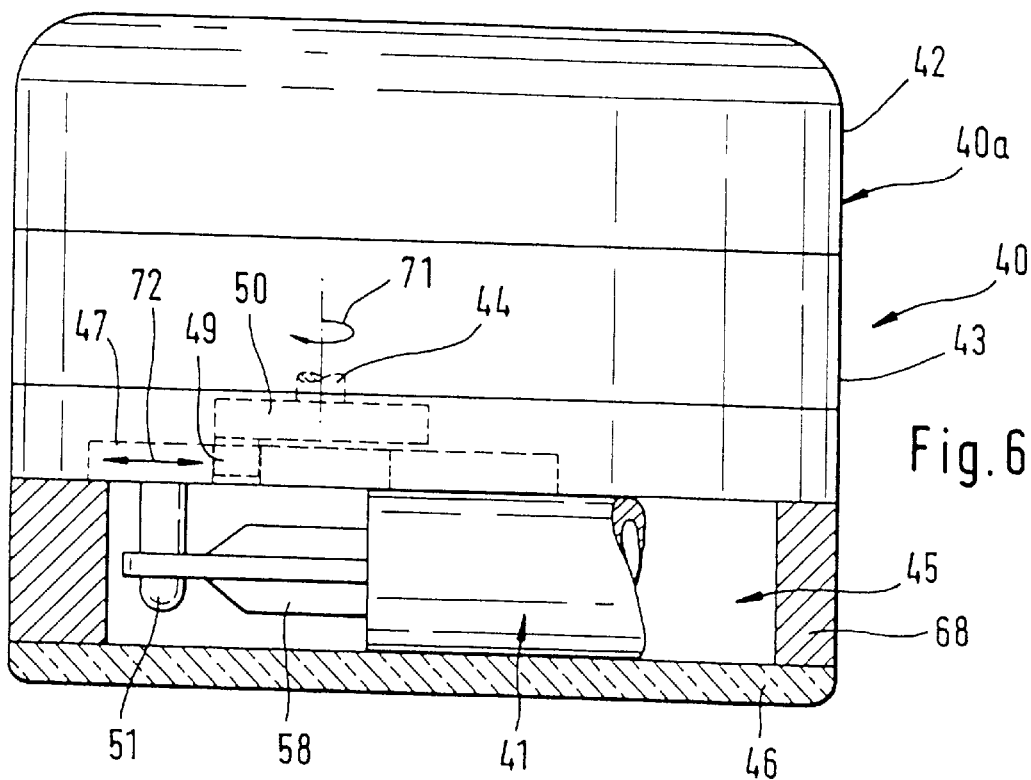
FIG. 6 shows an additional preferred embodiment of the dosing device.
Figure 7:
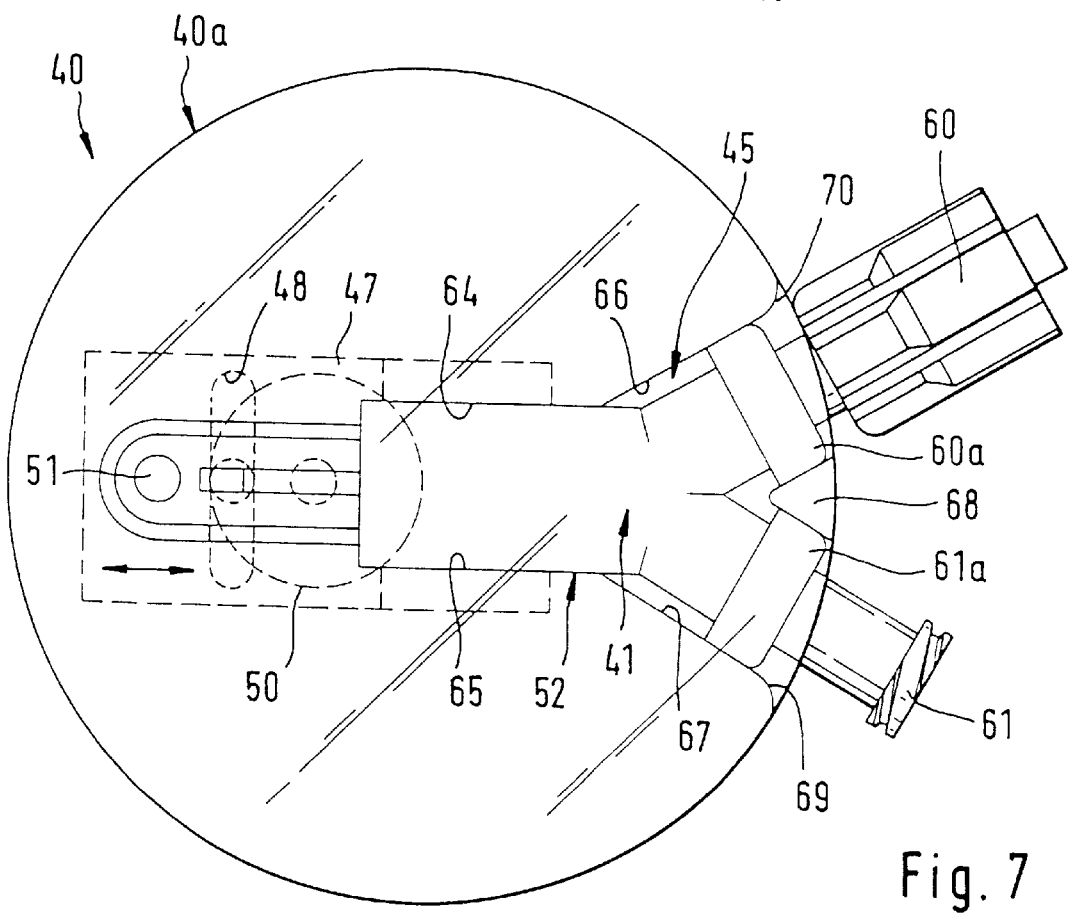
FIG. 7 shows a side view of the dosing device illustrated in FIG. 6, in a partial cross section.
Figure 8:
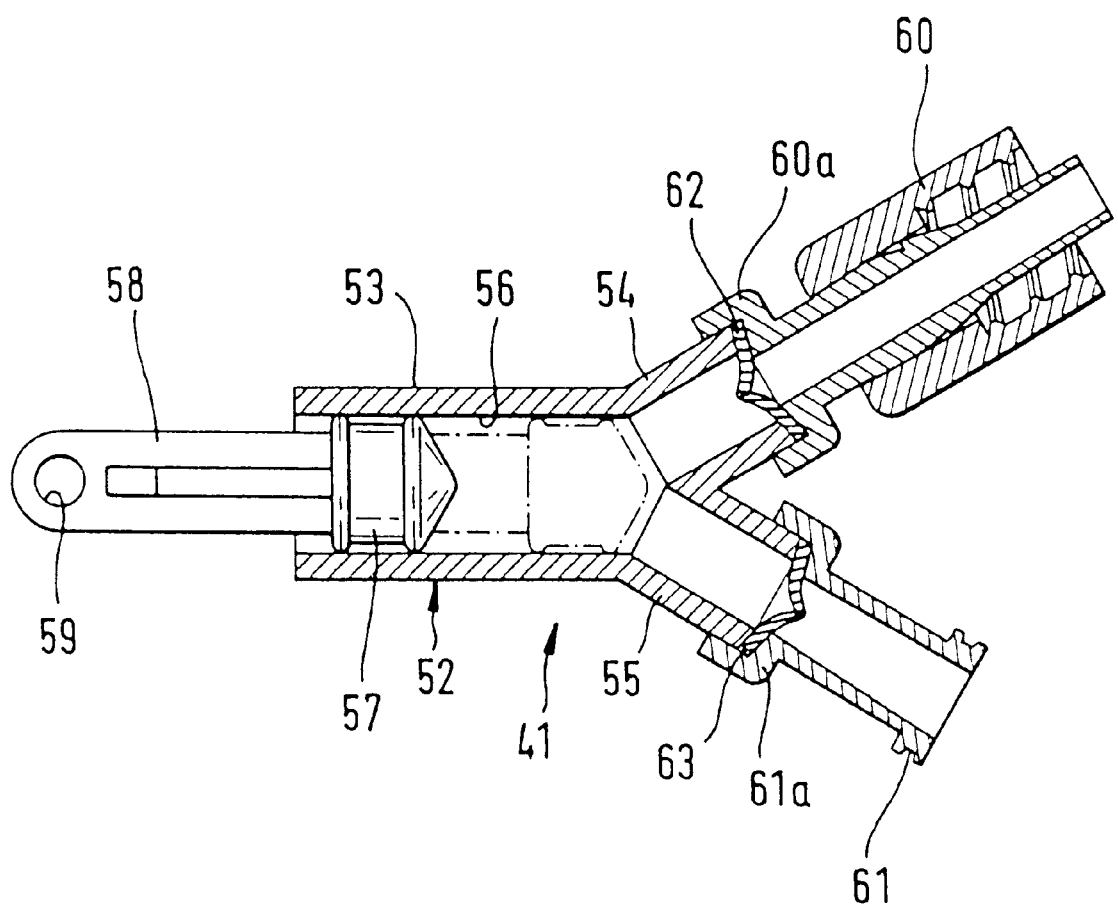
FIG. 8 shows the pump unit of the dosing device in a partial cross section.

FIGS. 6 to 8 illustrate an additional embodiment of the dosing device. The dosing device, as in the embodiment illustrated in FIGS. 1 to 5, consists of a drive unit 40 and a pump unit 41. The drive unit 40 has an essentially cylindrical housing part 40a, the upper housing half of which holds a motor 42 that is operated by a wind-up coil spring. The motor 42 has a transmission 43 with an output shaft 44. The spring-wound motor, which is similar to the motors used in timepieces and similar devices, and its transmission are shown only approximately and in no great detail. The lower half of the housing has a receptacle 45 in which the pump unit is loosely placed. The receptacle 45 is closed by a transparent base plate 46. Above the receptacle 45 there is a rectangular plate 47, which is guided so that it can move in the longitudinal direction. The plate 47 has a transverse slot 48 in which the projection 49 of a drive wheel 50 is engaged. The drive wheel 50 sits on the drive shaft 44 of the transmission 43. Fastened to the underside of the plate 47, which is guided so that it can move longitudinally, is a cylindrical pin 51 that projects into the receptacle 45 of the drive unit.

The pump unit 41 has a Y-shaped housing part 52, which is made of plastic, with one common leg 53 and two branching legs 54, 55. The common leg 53 forms a pump chamber 56 in which a piston 57 can move. Connected to the piston 57 is a piston rod 58, which on its free end has a cylindrical recess 59, the diameter of which is slightly larger than the diameter of the pin 51. The branching legs 54, 55 of the Y-shaped housing part form the inlet and outlet tubes of the pump unit 41. The inlet and outlet tubes 54, 55 have a Luer Lock outer cone 60 and the Luer Lock inner cone 61, respectively, to connect the Luer Lock connectors of the tubes to feeding systems of the prior art. Between the flange 60a of the outer cone 60 and the inlet tube 54 there is a gate-type inlet valve 62. A gate-type outlet valve 63 sits between the flange 61a of the inner cone 61 and the outlet tube 55.

The receptacle 45 of the drive unit 40 is bordered by two parallel contact surfaces 64, 65 which make a transition into the diagonal contact surfaces 66, 67. In the receptacle 45, the pump unit 41 is fixed in position by a triangular projection 68 that is in contact with the facing inner sides of the flanges 60a, 61a of the outer and inner cones 60, 61 respectively, whereby the inlet and outlet tubes 54, 55 with the outer and inner cones respectively extend outward through lateral recesses 69, 70 in the housing wall.

The pump unit 41 is inserted into the receptacle 45 of the drive unit 40 so that the pin of the slide is engaged in the recess 59 in the piston rod 58. When the drive unit 40 is put into operation, the output shaft 44 of the transmission rotates in the direction indicated by the arrow 71, so that the plate 47 with the pin 51 is moved back and forth in the direction indicated by the arrow 72. Because the pin 51 is engaged with the piston rod 58, the piston rod 58 is also moved back and forth. During the suction stroke, the pump chamber 56 is filled with fluid when the outlet valve 63 is closed and the inlet valve 62 is open, while in pressure operation, the fluid is transported when the inlet valve is closed and the outlet valve is open into the outlet tube 55. The delivery rate is thereby largely independent of the viscosity of the fluid and the volume of liquid in the reservoir.

After the dosing device has been used, the pump unit 41, which is realized in the form of a non-reusable, disposable item, can be removed from the receptacle 45 in the drive unit 40, and replaced with a new pump unit.

What is claimed is:

1. Device for dosing medicinal fluid, in particular a nutrient solution for enteral alimentation, having a pump unit comprising a housing part that has a pump chamber with an inlet and outlet, in which pump chamber there is a displacement element that transports the medicinal fluid, and a drive unit comprising a housing part that holds a drive system for the displacement element, characterized by the fact that the housing part (4, 52) that contains the pump chamber (12, 56) and the housing part (5, 40a) that contains the displacement element drive system (25, 27; 42, 43) can be separated from one another, whereby the displacement element (15, 57) and its drive system have coupling elements (22, 29; 51, 59) that, when the housing parts are joined, are engaged with one another so that the drive unit (3, 40) can be coupled to the pump unit (2, 41) and can be separated from the pump unit, and wherein the drive unit (3) has a motor (25) that can be operated by a wind-up coil spring.

2. Device as claimed in claim 1, characterized by the fact that the drive unit (3) has a transmission (27), the gear ratio of which can be adjusted.

3. Device as claimed in claim 1, characterized by the fact that the housing part (4) of the pump unit (2) has a connecting element (8), and the housing part (5) of the drive unit (3) has a complementary connecting element (23).

4. Device as claimed in claim 3, characterized by the fact that the connecting elements (8, 23) of the housing parts (4, 5) are realized in the form of screw threads.

5. Device as claimed in claim 1, characterized by the fact that the pump chamber (56) is essentially cylindrical, whereby the inlet and the outlet are located on one end of the pump chamber, that an inlet valve (62) is located in the inlet and an outlet valve (63) in the outlet, and that the displacement element is a piston (57) that can move in the pump chamber.

6. Device as claimed in claim 5, characterized by the fact that the piston (57) of the pump unit (41) has a piston rod (58) that projects out of the pump chamber (56) and has a recess (49), and that the drive unit (40) has a slide with a pin (51) that can move back and forth, and which is engaged in the recess in the piston rod when the drive unit is coupled.

7. Device as claimed in claim 1, characterized by the fact that the housing part (40a) of the drive unit (40) has a receptacle (45) into which the pump unit (41) can be inserted, so that the pump unit (41) is fixed in position in the receptacle.

8. Device as claimed in claim 7, characterized by the fact that the housing part (52) of the pump unit (41) is a Y-shaped tubular piece, whereby branching legs of the tubular piece form inlet and outlet tubes (54, 55) respectively.

9. Device as claimed in claim 8, characterized by the fact that a wall of the housing part (40a) of the drive unit (40) has a passage in the vicinity of the receptacle (45) so that the housing part (53) of the pump unit (41) with the inlet and outlet tubes (54, 55) which project out of the housing part of the drive unit, can be inserted into the receptacle of the drive unit.

10. Device as claimed in claim 1, characterized by the fact that the housing part (4) that contains the pump chamber (12) has two connectors (13, 14) for the connection of a feeding tube to the inlet (11) and outlet (10) of the pump chamber.

11. Feeding tube for the transport of a nutrient solution for enteral alimentation from a bag (29) that contains the nutrient solution to a stomach tube (32) that has a stomach tube hose (33) that is introduced into a patient's stomach, characterized by a device (1) in the feeding tube (30, 31) for dosing the nutrient solution as claimed in claim 1.

12. System for enteral alimentation with a bag (29) that contains a nutrient solution, a feeding tube (30, 31), and a stomach tube (32) that has a stomach tube hose (33), which is introduced into a patient's stomach, characterized by a device (1) in the feeding tube (30, 31) for dosing the nutrient solution as claimed in claim 1.

13. Device for dosing medicinal fluid, in particular a nutrient solution for enteral alimentation, having a pump unit comprising a housing part that has a pump chamber with an inlet and outlet, in which pump chamber there is a displacement element that transports the medicinal fluid, and a drive unit comprising a housing part that holds a drive system for the displacement element, characterized by the fact that the housing part (4, 52) that contains the pump chamber (12, 56) and the housing part (5, 40a) that contains the displacement element drive system (25, 27; 42, 43) can be separated from one another whereby the displacement element (15, 57) and its drive system have coupling elements (22, 29; 51, 59) that when the housing parts are joined, are engaged with one another so that the drive unit (3, 40) can be coupled to the pump unit (2, 41) and can be separated from the pump unit, and wherein the pump chamber (12) is essentially cylindrical, whereby the inlet (10) and the outlet (11) of the pump chamber (12) are offset from one another peripherally by 180°, and that the displacement element (15) is a rotating body in the pump chamber that has a plurality of wing-like displacement elements that are in tight contact with the wall of the cylinder.

14. Device as claimed in claim 13, characterized by the fact that the displacement element (15) has a central recess (22) that has an internal contour, and the drive unit (3) has an output shaft (29) that is provided with a corresponding external contour that is engaged in the recess in the displacement element when the drive unit is coupled.

* * * * *